(12) United States Patent  
Hüsler et al.

(10) Patent No.: US 7,307,192 B2
(45) Date of Patent: Dec. 11, 2007

(54) PROCESS FOR THE PREPARATION OF 1-PHENYLINDAN PHOTOINITIATORS

(75) Inventors: Rinaldo Hüsler, Basel (CH); Thomas Horni, Bärschwil (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 113 days.

(21) Appl. No.: 10/553,777

(22) PCT Filed: Apr. 26, 2004

(86) PCT No.: PCT/EP2004/050602

§ 371 (c)(1),
(2), (4) Date: Oct. 20, 2005

(87) PCT Pub. No.: WO2004/099111

PCT Pub. Date: Nov. 18, 2004

(65) Prior Publication Data

US 2006/0241323 A1   Oct. 26, 2006

(30) Foreign Application Priority Data

May 5, 2003   (EP) .................................. 03405314

(51) Int. Cl.
   *C07C 45/00*   (2006.01)
(52) U.S. Cl. ..................................................... 568/319
(58) Field of Classification Search ..................... None
   See application file for complete search history.

(56) References Cited

U.S. PATENT DOCUMENTS

| 4,987,159 A | 1/1991 | Li Bassi et al. ............... 522/36 |
| 2004/0116549 A1 | 6/2004 | Visconti et al. ............. 522/135 |
| 2005/0004249 A1 | 1/2005 | Fuchs et al. .................. 522/36 |

FOREIGN PATENT DOCUMENTS

WO    02/085832    10/2002

*Primary Examiner*—Sikarl A. Witherspoon
(74) *Attorney, Agent, or Firm*—Joseph C. Suhadolnik

(57) ABSTRACT

The invention relates to a process for the preparation of a crystalline isomeric mixture of compounds of formulae (I) and (II) which process comprises the following steps: a) the slow addition of aluminium chloride, in portions, to a solution comprising 1,1,3-trimethyl-3-phenylindan and isobutyric acid halide in a suitable solvent at a reaction temperature of from −20° C. to 20° C., an isomeric mixture consisting of compounds of formulae (Ia) and (IIa) being obtained; b) enol chlorination of compounds (Ia) and (IIa), an isomeric mixture consisting of compounds of formulae (Ib) and (IIb) being obtained; c) hydrolysis of the chlorinated isomeric mixture from step b). The invention relates also to the preparation of the individual compounds (I) and (II).

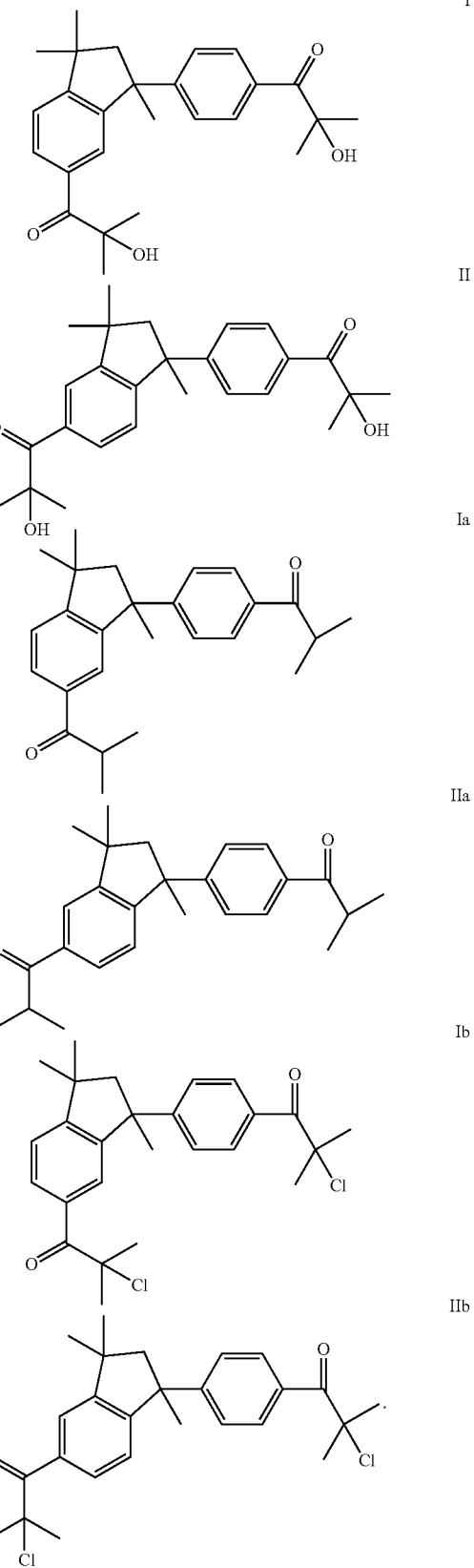

6 Claims, No Drawings

PROCESS FOR THE PREPARATION OF 1-PHENYLINDAN PHOTOINITIATORS

The invention relates to a novel process for the preparation of 1-phenylindan photoinitiators, especially of 2-hydroxy-1-{3-[4-(2-hydroxy-2-methyl-propionyl)-phenyl]-1,1,3-trimethyl-indan-5-yl}-2-methyl-propan-1-one and 2-hydroxy-1-{1-[4-(2-hydroxy-2-methyl-propionyl)-phenyl-[1,3,3-trimethyl-indan-5-yl}-2-methyl-propan-1-one.

U.S. Pat. No. 4,987,159 describes a process for the preparation of the above-mentioned mixture by Friedel-Crafts acylation of 1,1,3-trimethyl-3-phenylindan using isobutyric acid chloride in methylene chloride. The corresponding bis-isopropyl ketone is formed and is chlorinated using sulfuryl chloride. Subsequent hydrolysis with sodium methanolate and then with dilute hydrochloric acid yields a mixture of 2-hydroxy-1-{3-[4-(2-hydroxy-2-methyl-propionyl)-phenyl]-1,1,3-trimethyl-indan-5-yl}-2-methyl-propan-1-one and 2-hydroxy-1-{1-[4-(2-hydroxy-2-methyl-propionyl)phenyl]-1,3,3-trimethyl-indan-5-yl}-2-methyl-propan-1-one. The product is wax-like and tacky and contains small amounts of oligomeric compounds, which inhibit successful crystallisation. Purification of the tacky product can be carried out by means of column chromatography.

WO 02/0855832 describes the above-mentioned mixture of 2-hydroxy-1-{3-[4-(2-hydroxy-2-methyl-propionyl-phenyl]-1,1,3-trimethyl-indan-5-yl}-2-methyl-propan-1-one and 2-hydroxy-1{-1-[4-(2-hydroxy-2-methyl-propionyl)-phenyl]-1,3,3-trimethyl-indan-5-yl}-2-methyl-propan-1-one as a constituent of a solid mixture of alpha-hydroxy-carbonyl derivatives of alpha-methyl-styrene oligomers.

The object of the present invention was to provide a pulverulent crystalline product largely devoid of oligomeric constituents.

The object was achieved by the process described hereinbelow.

Process for the preparation of a crystalline isomeric mixture of compounds of formulae I and II

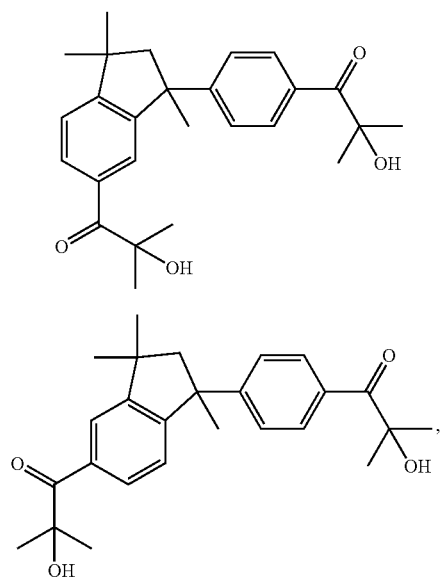

which process comprises the following steps:

a) the slow addition of aluminium chloride, in portions, to a solution comprising 1,1,3-trimethyl-3-phenylindan and isobutyric acid halide in a suitable solvent at a reaction temperature of from −20° C. to 20° C., an isomeric mixture consisting of compounds of formulae Ia and IIa being obtained

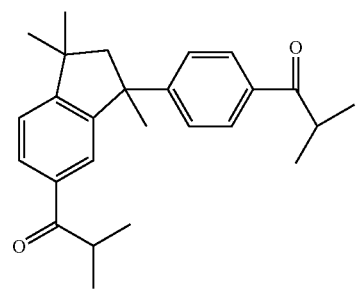

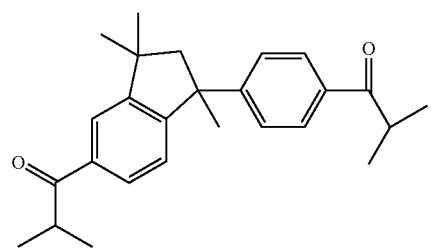

b) enol chlorination of compounds Ia and IIa, an isomeric mixture consisting of compounds of formulae Ib and IIb being obtained

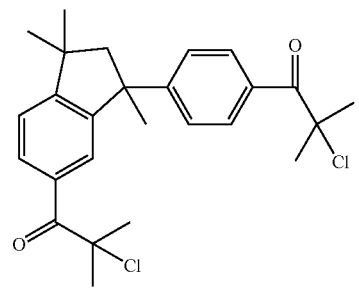

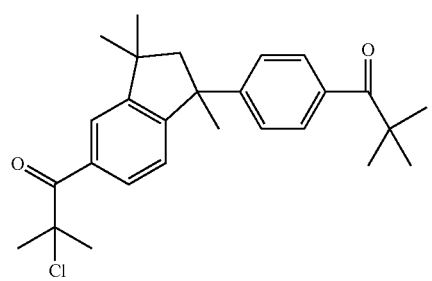

c) hydrolysis of the chlorinated isomeric mixture from step b).

The following reaction scheme gives an overview of the reaction steps.

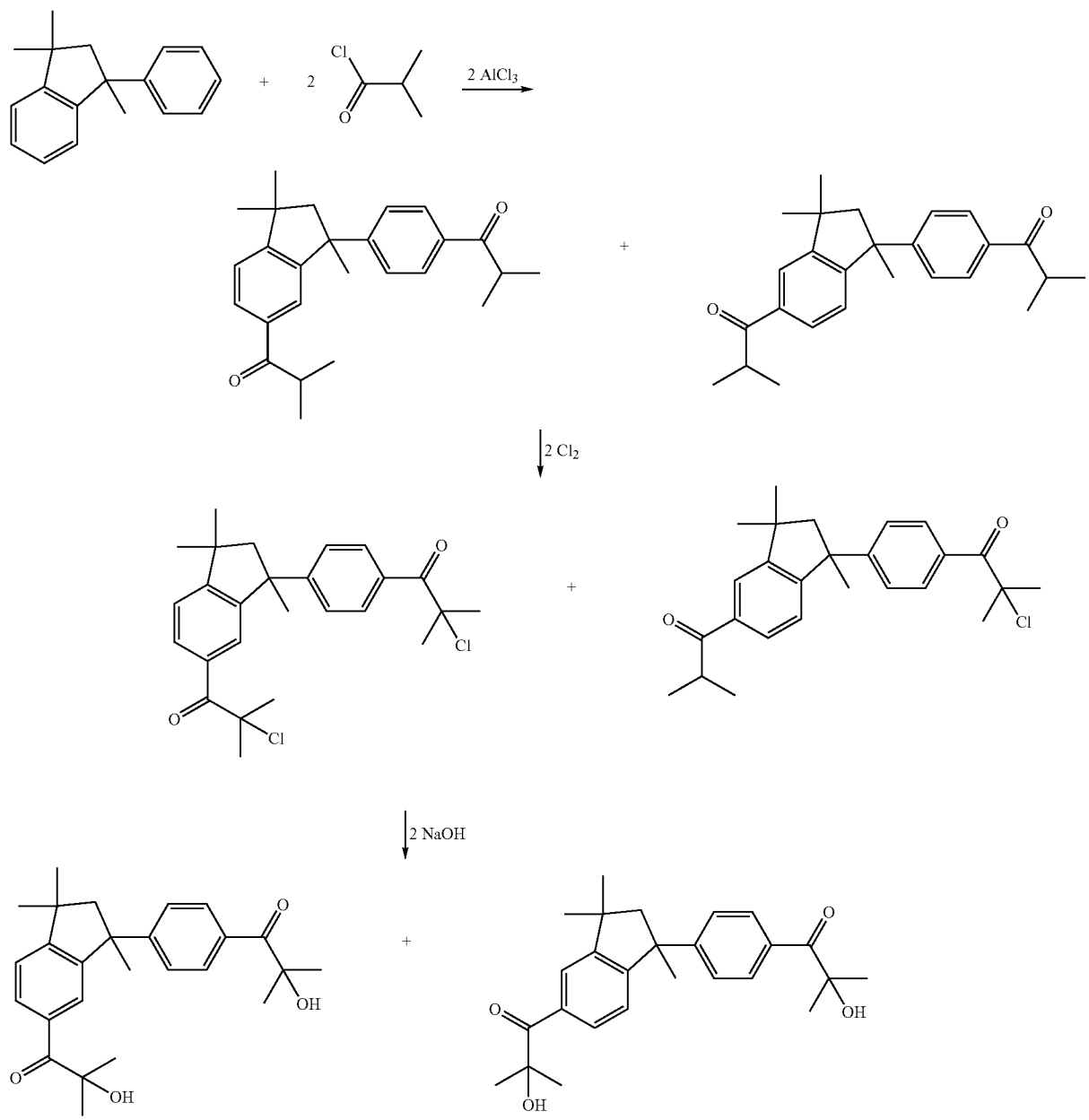

Important factors in reaction step a) are the use of pure 1,1,3-trimethyl-3-phenylindan having a low oligomer content, the choice of solvent, the slow metered addition of aluminium chloride and the maintenance of a temperature below 20° C. Above 20° C., the isobutyric acid chloride slowly decomposes with the liberation of CO and yields additional isopropyl derivatives in the Friedel-Crafts reaction.

Any solvents that are inert under the given reaction conditions are possible, for example ethylene chloride, trichoroethylene, methylene chloride, tetrachloroethane, chlorobenzene, bromobenzene, dichlorobenzene, cydohexane, methylcydohexane, carbon disulfide, nitromethane, nitroethane, nitropropane and nitrobenzene. Chlorobenzene or 1,2-dichlorobenzene is preferred.

A solvent that is especially preferred is 1,2-dichlorobenzene. Although methylene chloride is possible in this reaction, it is less suitable because it participates in the reaction to a small extent, leading to the formation of oligomeric compounds which interfere with the crystallisation process.

The metered addition of aluminium chloride must be carried out slowly, for example over a period of from 2 to 3 hours. It is important to avoid a local overdosing of aluminium chloride, because a high aluminium chloride concentration causes the starting material 1,1,3-trimethyl-3-phenylindan to isomerise, which likewise leads to the formation of oligomeric compounds.

Aluminium chloride can be added in solid form or in solution in isobutyric acid chloride and chlorobenzene or 1,2-dichlorobenzene as diluent.

The sequence of the addition of the reagents is important for the success of the reaction. The best product qualities are obtained when 1,1,3-trimethyl-3-phenylindan and isobutyric acid halide are first brought together and aluminium chloride is slowly metered in. The prior addition of the acid chloride buffers the action of the aluminium chloride and accordingly suppresses oligomer formation. In a variant, the aluminium chloride can be dissolved in the liquid acid halide and then added dropwise to the aromatic compound.

In the isomeric mixture of compounds of formulae Ia and IIa, the compound of formula Ia is the main component with a content of about 60%.

The reaction temperature in step a) is from −20° C. to 20° C., preferably from 0° C. to 10° C. especially from 0° C. to 5° C.

From 1.8 to 2.8 equivalents, preferably from 2.0 to 2.6 equivalents, especially from 2.2 to 2.4 equivalents, of isobutyric acid chloride, based on 1,1,3-trimethyl-3-phenylindan, are used.

The ketone of step (a) is obtained in the form of an isomeric mixture and can be chlorinated in step (b) directly without being isolated. Chlorinating agents are sulfuryl chloride or chlorine gas. The chlorination is preferably carried out by the introduction of chlorine gas at a temperature of from 20 to 90° C., preferably from 50 to 60° C.

Subsequent hydrolysis with aqueous alkali metal hydroxide (step c) yields a mixture of 2-hydroxy-1-{3-[4-(2-hydroxy-2-methyl-proplonyl)phenyl]-1,1,3-trimethyl-indan--5-yl}-2-methyl-propan-1-one and 2-hydroxy-1-{1-[4-(2-hydroxy-2-methyl-propionyl)-phenyl]-1,3,3-trimethyl-indan-5-yl}-2-methyl-propan-1-one dissolved in the organic phase. In order to carry out the hydrolysis more rapidly it is advantageous to use a mixture of methanol and water and subsequently acidify the reaction solution. The hydrolysis product is crystallised from a suitable solvent, for example toluene. The concentrated filtrates (mother liquors) also exhibit activity.

When chlorination and cooling of the reaction solution are complete (step b), the reaction solution begins to crystallise. Separation of the isomers can be carried out by recrystallisation, for example from cyclohexane.

There is obtained isomerically pure 2-chloro-1-{3-[4-(2-chloro-2-methyl-proplonyl)-phenyl]-1,1,3-trimethyl-indan-5-yl}-2-methyl-propan-1-one (formula Ib), which can be hydrolysed separately. After the hydrolysis, the crystalline compound of formula I is obtained.

The crystalline compound of formula II is prepared from the mother liquor by hydrolysis.

The invention accordingly relates also to a process for the preparation of a crystalline compound of formula I

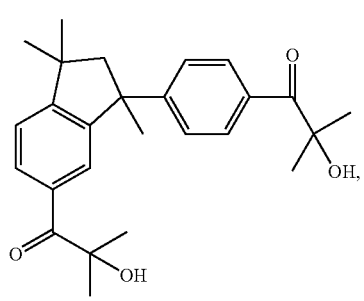

which process comprises the following steps:

a) the slow addition of aluminium chloride, in portions, to a solution comprising 1,1,3-trimethyl-3-phenylindan and isobutyric acid halide in a suitable solvent at a reaction temperature of from −20° C. to 20° C., an isomeric mixture consisting of compounds of formulae Ia and IIa being obtained

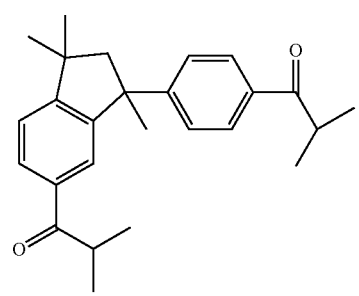

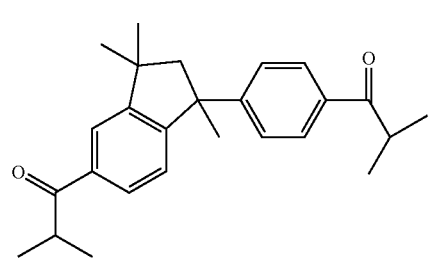

b) enol chlorination of compounds Ia and IIa, an isomeric mixture consisting of compounds of formulae Ib and IIb being obtained

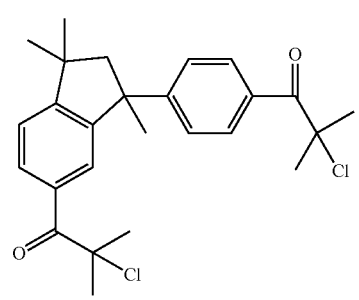

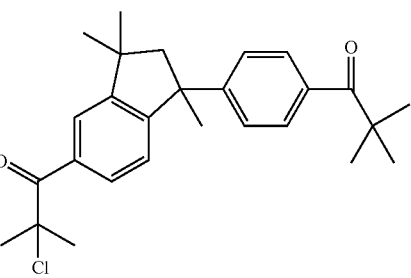

c) separation of the compound of formula Ib by recrystallisation d) hydrolysis of compound Ib.

The invention relates also to a process for the preparation of a crystalline compound of formula II

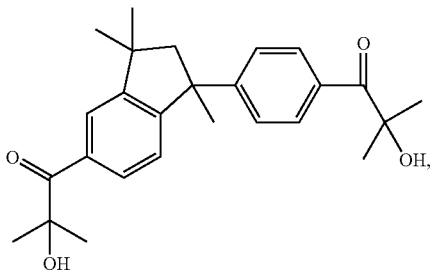

I which process comprises the following steps:

a) the slow addition of aluminium chloride, in portions, to a solution comprising 1,1,3-trimethyl-3-phenylindan and isobutyric acid halide in a suitable solvent at a reaction temperature of from −20° C. to 20° C., an isomeric mixture consisting of compounds of formulae Ia and IIa being obtained

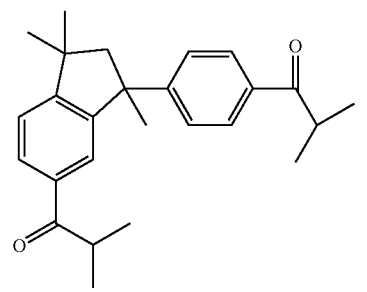

Ia

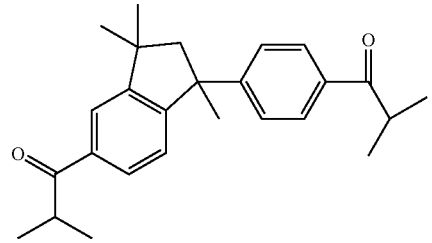

IIa b) enol chlorination of compounds Ia and IIa, an isomeric mixture consisting of compounds of formulae Ib and IIb being obtained

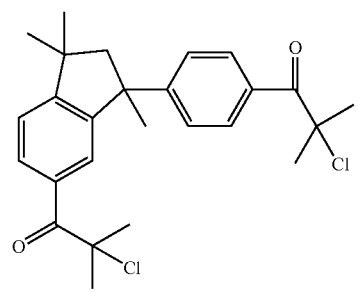

Ib

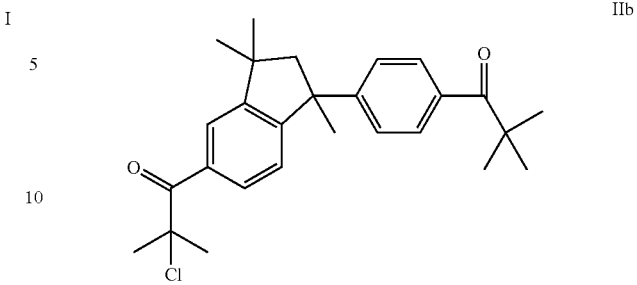

IIb c) separation of the compound of formula Ib by recrystallisation d) hydrolysis of compound IIb.

The crystalline isomeric mixture of (compounds of formulae I and II) and the crystalline isomerically pure compounds are suitable as photoinitiators. Preferred applications are in pigmented and non-pigmented surface coatings, overprint coatings, powder coatings, printing inks, gel coats, composite materials or glass fibre coatings. Application in non-pigmented coatings is much more important than in pigmented coatings, because the product is subject to only a small amount of yellowing.

The following Examples illustrate the novel preparation process in detail.

EXAMPLE 1

1.1) Friedel-Crafts reaction addition of $AlCl_3$ in solid form 153.6 g (0.65 mol) of 1,1,3-trimethyl-3-phenylindan (from Schenectady Pratteln Switzerland), 159.3 g (1.495 mol) of isobutyric acid chloride and 195 g of 1,2-dichlorobenzene are placed in a 750 ml reaction flask and cooled to 5-0° C. by means of an ice bath. In the course of about two to three hours, 208.0 g (1.56 mol) of aluminium chloride are then added in small portions at an internal temperature of 5-0° C. HCl gas is evolved. Stirring is then carried out for about 16 hours at an internal temperature of 0-5° C. At the end of that period, all the aluminium chloride has dissolved. The reddish reaction mixture is then poured onto ice and water and stirred to complete the reaction. The two phases are separated in a separating funnel. The organic phase is washed with water and then concentrated for a short time in a vacuum rotary evaporator at about 60° C. and about 25 mbar. There are obtained 413 g of yellowish oil, an isomeric mixture having 1-[3-(4-isobutyryl-phenyl1,1,3-trimethyl-indan-5-yl]-2-methyl-propan-1-one as the main component and 1-[1-(4-isobutyryl-phenyl)-1,3,3-trimethyl-indan-5-yl]-2-methyl-propan-1-one as the subsidiary component dissolved in 1,2-dichlobenzene. Excluding the solvent 1,2-dichlorobenzene, about 60% of the main component and about 40% of the subsidiary component are found in the GC and $^1$H-NMR spectrum. The isomeric mixture is used in the next reaction without being purified further.

1.2) Enol Chlorination 413 g (0.65 mol tq) of the solution of the isomeric mixture from the Friedel-Crafts reaction having 1-[3-(4-isobutyryl-phenyl)-1,1,3-trimethyl-indan-5yl]-2-methyl-propan-1-one as the main component and 1-[1-(4-isobutyryl-phenyl)-1,3,3-trimethyl-indan-5-yl]-2-methyl-propan-1-one as the subsidiary component are placed in a 750 ml reaction flask and heated to 55-60° C. by means of an oil bath. Then, at 55-60°

C., with thorough stirring, 92.2 g (1.30 mol) of chlorine gas are introduced through a glass frit, relatively quickly at the start and just slowly at the end. HCl gas is evolved. The duration of the introduction is about five to six hours. The reaction is monitored by means of the ¹H-NMR spectrum. Cooling is then carried out and the reaction solution begins to crystallise. The slightly yellowish suspension is cooled to about 5° C. and filtered. The crystals are washed with 154 g of mixed hexanes and dried in vacuo. 160 g of white crystals are obtained. An 80 g sample is recrystallised with three times the amount of cyclohexane. 66.3 g of white crystals are obtained. According to the ¹H-NMR spectrum they are isomerically pure 2-chloro-1-{3-[4-(2-chloro-2-methyl-proplonyl)-phenyl]-1,3,3-trimethyl-indan-5-yl}-2-methyl-propan-1-one and they melt at 142.5-143.5° C.

Elemental Analysis: (455.43)

|  | % C |  | % H |  | % Cl |
|---|---|---|---|---|---|
| calculated: | 70.11 | calculated: | 6.79 | calculated: | 15.92 |
| found: | 70.05 | found: | 6.86 | found: | 16.00 |

The mother liquor, 317 g of yellowish solution with mixed hexanes and 1,2-dichlorobenzene, is concentrated and distilled. 179 g tq of yellowish solution remain. According to the ¹H-NMR spectrum the subsidiary component 2-chloro-1-{1-[4-(2-chloro-2-methyl-proplonyl)-phenyl]-1,3,3methyl-indan-5-yl}-2-methyl-propan-1-one is enriched therein (about 81% to 19%). The 179 g of solution are used in the next reaction without being purified further.

1.3) Hydrolysis of the subsidiary component 2chloro-1-{1-[4-(2-chloro-2-methyl-propionyl)-phenyl]-1,3,3-trimethyl-indan-5-yl}-2-methyl-propan-1-one from the chlorination 93.3 g (0.70 mol) of 30% concentrated NaOH and 93 ml of deionised water and 92 g of methanol are combined in a 750 ml reaction flask. There are then added dropwise at 50° C. in the course of about 30 minutes, with thorough stirring, 179 g (0.2908 mol tq) of a solution, in 1,2-dichlorobenzene, of the subsidiary component 2chloro-1-{1-[4-(2-chloro-2-methyl-proplonyl)pheny]-1,3,3-trimethyl-indan-5-yl}-2-methyl-propan-1-one from the preceding chlorination reaction, additionally diluted with 46 g of methanol. The internal temperature slowly rises to 55-60° C. The orange alkaline mixture (about pH 12) is then stirred for about three to four hours at 55-60° C. The conversion is checked with a GC sample and a ¹H-NMR sample. The mixture is then cooled to 45° C. and adjusted dropwise to a pH of about 1-2 with about 37 g of 16% hydrochloric acid. The colour of the emulsion changes from yellow to pale yellow. The mixture is then stirred for about one hour at 60° C. When the hydrolysis is complete, the reaction mixture is neutralised with a small amount of dilute sodium hydroxide solution. The two phases are separated at about 25° C. in a separating funnel. The organic phase is concentrated in a rotary evaporator. There are obtained 179.4 g of oil, which is subjected to steam distillation in order to remove the 1,2-dichlorobenzene. At the end of the distillation, 114.2 g of yellow viscous oil are obtained. This corresponds to a tq yield of 96% of theory (408.54) over all three reaction steps. A 30 g sample is stirred with 30 g of diethyl ether and seeded. The crystals are filtered off, washed and dried. There are obtained 10 g of white crystals, which melt at 124.0-125.5° C. In the ¹H-NMR spectrum, the isomerically pure subsidiary component 2-hydroxy-1-{1-[4-(2-hydroxy-2-methyl-propionyl)-phenyl]-1,3,3-trimethyl-indan-5-yl}-2-methyl-propan-1-one is found.

Elemental Analysis: (408.54)

|  | % C |  | % H |
|---|---|---|---|
| calculated: | 76.44 | calculated: | 7.90 |
| found: | 76.31 | found: | 7.92 |

A sample of those crystals is again crystallised from toluene, and the white crystals then melt at 125.5-127.8° C.

Elemental Analysis: (408.54).

|  | % C |  | % H |
|---|---|---|---|
| calculated: | 76.44 | calculated: | 7.90 |
| found: | 76.59 | found: | 7.84 |

1.4) Hydrolysis of the main component 2-chloro-1-{3-[4-(2-chloro-2-methyl-proplonyl)-phenyl]-1,1,3-trimethyl-indan-5-yl}-2-methyl-propan-1-one from the chlorination 47.4 g (0.356 mol) of 30% concentrated NaOH and 47 ml of deionised water and 47 g of methanol are combined in a 500 ml reaction flask. There are then added dropwise at 50° C. in the course of about 30 minutes, with thorough stirring, 66.0 g (0.1482 mol) of recrystallised main component 2-chloro-1-{3-[4-(2-chloro-2-methyl-proplonyl)-phenyl]-1,1,3-trimethyl-indan-5-yl}-2-methyl-propan-1-one from the preceding chlorination reaction, dissolved in 190 g of toluene and 23 g of methanol in the warm state. The internal temperature slowly rises to 54° C. The alkaline emulsion (about pH 12) is then stirred at 55-60° C. The conversion is checked with a GC sample and a ¹H-NMR sample. 60 g of methanol are then additionally added in two portions, in order to accelerate the reaction. The duration of the hydrolysis is about five to six hours. The mixture is then cooled to 35° C. and adjusted dropwise to a pH of about 1-2 with about 15 g of 16% hydrochloric acid. The colour of the emulsion lightens to pale yellow. The mixture is then stirred for about one hour at 60° C. When the hydrolysis is complete, the reaction mixture is neutralised with a small amount of dilute sodium hydroxide solution. The two phases are separated at about 25° C. in a separating funnel. The organic phase is concentrated in a rotary evaporator. It crystallises spontaneously. The crystals are dried without being purified further. There are obtained 60.2 g of white crystals, which melt at 116.5-118.5° C. This corresponds to a tq yield of 99% of theory (408.54) over the last reaction step and a tq yield of 82% of theory (408.54) over all three reaction steps. In the ¹H-NMR spectrum, the isomerically pure main component 2-hydroxy-1-{3-[4-(2-hydroxy-2-methyl-propionyl)phenyl]-1,1,3-trimethyl-indan-5-yl}-2-methyl-propan-1-one is found.

EXAMPLE 2

2.1) Friedel-Crafts reaction A portion of the AlCl₃ is added dropwise in dissolved form 90 g (0.845 mol) of isobutyric acid chloride and 70 g of 1,2-dichlorobenzene are placed in a 500 ml reaction flask and cooled to 5-0° C. by means of an ice bath. In the course of about 20 minutes, 66.7 g (0.50 mol) of aluminium chloride are then added in small portions at an internal temperature of 5-0° C. The dissolution process is slightly exothermic. The yellowish solution is kept at an internal temperature of 5-0° C.

100.0 g (0.423 mol) of 1,1,3-trimethyl-3-phenylindan (from Schenectady Prattein Switzerland), 13.7 g (0.128 mol) of isobutyric acid chloride and 100 g of 1,2-dichlorobenzene are placed in a 750 ml reaction flask and cooled to 5-0° C. by means of an ice bath. The aluminium chloride solution is then added dropwise in the course of 90 minutes at an internal temperature of 5-0° C. The solution becomes yellow and HCl gas is evolved. About 1% starting material is then found in the GC in addition to the mono compound. A further 68.7 g (0.515 mol) of aluminium chloride are then added in small portions in the course of one hour at an internal temperature of 5-0° C. HCl gas is further evolved. The suspension is then stirred for about 20 hours at an internal temperature of 0-5° C. The reaction conversion is monitored by means of GC. At the end of that period, all the aluminium chloride has dissolved. The red reaction mixture is then poured onto ice and water and stirred to complete the reaction. The two phases are separated in a separating funnel. The organic phase is washed with water and then concentrated for a short time in a vacuum rotary evaporator at about 60° C. and about 25 mbar. There are obtained 357.8 g of a reddish liquid, an isomeric mixture having 1-[3-(4-isobutyryl-phenyly-1,1,3-trimethyl-indan-5-yl]-2-methyl-propan-1-one as the main component and 1-[3-(4-isobutyryl-phenyl)-1,3,3-trimethyl-indan-5-yl]-2-methyl-propan-1-one as the subsidiary component, dissolved in 1,2-dichlorobenzene. Excluding the solvent 1,2-dichlorobenzene, about 60% of the main component and about 40% of the subsidiary component are found in the GC and $^1$H-NMR spectrum. The isomeric mixture is used in the next reaction without being purified further.

2.2) Enol Chlorination 322.0 g (0.3807 mol tq) of the solution of the isomeric mixture from the Friedel-Crafts reaction having 1-[3-(4-isobutyryl-phenyl)-1,1,3-trimethyl-indan-5-yl]-2-methyl-propan-1-one as the main component and 1-[1-(4-isobutyryl-phenyl)-1,3,3-trimethyl-indan-5-yl]-2-methyl-propan-1-one as the subsidiary component are placed in a 750 ml reaction flask and heated to 55-60° C. by means of an oil bath. Then, at 55-60° C., with thorough stirring, 56.0 g (0.79 mol) of chlorine gas are introduced through a glass frit, relatively quickly at the start and just slowly at the end. HCl gas is evolved. The duration of the introduction is about six to seven hours. The reaction is monitored by means of the $^1$H-NMR spectrum. Cooling is then carried out and the reaction solution begins to crystallise. The white suspension is cooled to about 5° C. and filtered. The crystals are washed with 110 g of mixed hexanes and, while still moist (about 81 g), are recrystallised from 260 g of cyclohexane, filtered, washed and dried. 68.7 g of white crystals are obtained. This corresponds to a partial yield of 40.5% of theory (445.43) over two reaction steps. According to the $^1$H-NMR spectrum they are isomerically pure 2-chloro-1-{3-[4-(2-chloro-2-methyl-propionyl)-phenyl]-1,1,3-trimethyl-indan-5-yl}-2-methyl-propan-1-one and they melt at 142.5-143.7° C.

The mother liquors are collected and concentrated in vacuo. Water is added to the residue, 277.5 g of yellowish oil, and 1,2-dichlorobenzene is removed by steam distillation. The viscous yellowish residue Is dissolved at about 60° C. in 125 g of mixed hexanes, cooled and seeded. The crystals are filtered off, washed with mixed hexanes and dried. There are obtained 22.7 g of pale beige crystals, which melt at 110-119° C. According to the $^1$H-NMR spectrum they are no longer isomerically pure. The mother liquor is concentrated and yields 83.5 g tq of yellow oil. According to the $^1$H-NMR spectrum the subsidiary component 2-chloro-1-{1-[4-(2-chloro-2-methyl-propionyl)-phenyl]-1,3,3-trimethyl-indan-5-yl}-2-methyl-propan-1-one is enriched therein (about 83% to 17%). The 83.5 g of yellow oil are used in the next reaction without being purified further.

The 22.7 g of crystals are recrystallised from 88 g of cydohexane, filtered and dried. There are obtained 9.0 g of white crystals, which melt at 135-140° C. According to the $^1$H-NMR spectrum they are a mixture of 91% of the main component 2-chloro-1-{3-[4-(2-chloro-2-methyl-proplonyl)-phenyl]-1,1,3-trimethyl-indan-5yl}-2-methyl-propan-1-one and 9% of the subsidiary component 2-chloro-1-{1-[4-(2-chloro-2-methyl-propionyl)-phenyl]-1,3,3-trimethyl-indan-5-yl}-2-methyl-propan-1-one. In the concentrated mother liquor, 12.0 g of a yellow viscous oil, the subsidiary component 2-chloro-1-{1-[4-(2-chloro-2-methyl-proplonyl)-phenyl]-1,3,3-trimethyl-indan-5-yl}-2-methyl-propan-1-one is enriched (about 67% to 33%).

2.3) Hydrolysis of the subsidiary component 2-chloro-1-{1-[4-(2-chloro-2-methyl-proplonyl)-phenyl]-1,3,3-trimethyl-indan-5-yl}-2-methyl-propan-1-one from the chlorination 56.0 g (0.42 mol) of 30% concentrated NaOH and 56 ml of deionised water and 55 g of methanol are combined in a 750 ml reaction flask. There are then added dropwise at 55° C. in the course of about 30 minutes, with thorough stirring, 83.0 g (0.1745 mol tq) of oil of the subsidiary component 2-chloro-1-{1-[4-(2-chloro-2-methyl-propionyl)-phenyl]-1,3,3-trimethyl-indan-5-yl}-2-methyl-propan-1-one from the preceding chlorination reaction, additionally diluted with 200 g of toluene and with 29 g of methanol. The internal temperature remains at 55-60° C. The yellowish-orange alkaline emulsion (about pH 11) is then stirred for about five to six hours at 55-60° C. The conversion is checked with a GC sample and a $^1$H-NMR sample. The mixture is then cooled to 40° C. and adjusted dropwise to a pH of about 1-2 with about 25 g of 16% hydrochloric acid. The colour of the emulsion changes from yellow to pale yellow. The mixture is then stirred for about one hour at 60° C. When the hydrolysis is complete, the reaction mixture is neutralised with a small amount of dilute sodium hydroxide solution. The two phases are separated at about 25° C. in a separating funnel. The organic phase is concentrated in a vacuum rotary evaporator. There are obtained 77.7 g of oil. 100 g of diethyl ether are added to the oil, followed by heating and seeding with crystals. A portion crystallises out overnight. The suspension is cooled to about 0° C. and filtered. The crystals are washed with 30 g of diethyl ether and dried. There are obtained 15.7 g of white crystals, which melt at 122.0-124.5° C. In the $^1$HMR spectrum, the isomerically pure subsidiary component 2-hydroxy-1-{1-[4-(2-hydroxy-2-methyl-proplonyl)-phenyl]-1,3,3-trimethyl-indan-5-yl}2-methyl-propan-1-one is found. The mother liquor is concentrated and there are obtained 58 g of yellowish oil which, according to the $^1$H-NMR spectrum, is an isomeric mixture.

2.4) Hydrolysis of the main component 2-chloro-1-{3-[4-(2-chloro-2-methyl-proplonyl)-phenyl]-1,1,3-trimethyl-indan-5-yl}-2-methyl-propan-1 -one from the chlorination 48.0 g (0.36 mol) of 30% concentrated NaOH and 48 ml of deionised water and 48 g of methanol are combined in a 500 ml reaction flask. There are then added dropwise at 50° C. in the course of about 45 minutes, with thorough stirring, 66.8 g (0.150 mol) of the recrystallised main component, 2-chloro-1-{3-[4-(2-chloro-2-methyl-propionyl)-phenyl]-1,1,3-trimethyl-indan-5-yl}-2-methyl-propan-1-one, from the preceding chlorination reaction, dissolved in 190 g of toluene and 83 g of methanol in the warm state. The internal temperature slowly rises to 56° C. The alkaline emulsion (about pH 11) is then stirred at 55-60° C. The conversion is checked with a GC sample and a ¹H-NMR sample. The duration of the hydrolysis is about four to five hours. The mixture is then cooled to 35° C. and adjusted dropwise to a pH of about 1-2 with about 16.4 g of 16% hydrochloric acid. The colour of the emulsion lightens. The mixture is then stirred for about one hour at 60° C. When the hydrolysis is complete, the reaction mixture is neutralised with a small amount of dilute sodium hydroxide solution. The two phases are separated at about 40° C. in a separating funnel. The organic phase is concentrated in a rotary evaporator. There are obtained 65.0 g of colourless viscous oil, which slowly crystallises. The crystals are recrystallised from 100 g of toluene and dried. There are obtained 54.9 g of white crystals, which melt at 117.7-119.0° C. This corresponds to a tq yield of 90% of theory (408.54) over the last reaction step. In the ¹H-NMR spectrum, the isomerically pure main component 2-hydroxy-1-{3-[4-(2-hydroxy-2-methyl-propionyl)-phenyl]-1,1,3-trimethyl-indan-5-yl}-2-methyl-propan-1-one is found.

Elemental Analysis: (408.54)

|  | % C |  | % H |
|---|---|---|---|
| calculated: | 76.44 | calculated: | 7.90 |
| found: | 76.26 | found: | 7.88 |

A sample of those crystals is again crystallised from toluene, and the white crystals then melt at 117.8-119.0° C. Concentration of the mother liquor yields a further 6.1 g of colourless highly viscous oil. According to the ¹H-HMR spectrum, there are about 75% of the main component and about 25% of the subsidiary component therein.

Elemental Analysis: (408.54)

|  | % C |  | % H |
|---|---|---|---|
| calculated: | 76.44 | calculated: | 7.90 |
| found: | 76.32 | found: | 7.84 |

EXAMPLE 3

3.1) Friedel-Crafts reaction Addition of AlCl₃ in solid form 153.6 g (0.65 mol) of 1,1,3-trimethyl-3-phenylindan (from Schenectady Prattein Switzerland), 159.3 g (1.495 mol) of isobutyric acid chloride and 203 g of 1,2-dichlorobenzene are placed in a 750 ml reaction flask and cooled to 5-0° C. by means of an ice bath. In the course of about two to three hours, 208.0 g (1.56 mol) of aluminium chloride are then added in small portions at an internal temperature of 5-0° C. HCl gas is evolved. Stirring is then carried out for about 17 hours at an internal temperature of 0-5° C. At the end of that period, all the aluminium chloride has dissolved. The reddish reaction mixture is then poured onto ice and water and stirred to complete the reaction. The two phases are separated in a separating funnel. The organic phase is washed with water and then concentrated for a short time in a vacuum rotary evaporator at about 60° C. and about 25 mbar. There are obtained 572 g of reddish oil, an isomeric mixture having 1-[3-(4-isobutyryl-phenyl)-1,1,3-trimethyl-indan-5-yl]-2-methyl-propan-1-one as the main component and 1-[1-(4-isobutyryl-phenyl)-1,3,3-trimethyl-indan-5-yl]-2-methyl-propan-1-one as the subsidiary component, dissolved in 1,2-dichloro-benzene. Excluding the solvent 1,2-dichlorobenzene, about 60% of the main component and about 40% of the subsidiary component are found in the GC and ¹H-NMR spectrum. The isomeric mixture is used in the next reaction without being purified further.

3.2) Enol Chlorination 572 g (0.65 mol tq) of the solution of the isomeric mixture from the Friedel-Crafts reaction having 1-[3-(4-isobutyryl-phenyl)1,1,3-trimethyl-indan-5-yl]-2-methyl-propan-1-one as the main component and 1-[1-(4-isobutyryl-phenyl)-1,3,3-trimethyl-indan-5-yl]-2-methyl-propan-1-one as the subsidiary component are placed in a 750 ml reaction flask and heated to 55-60° C. by means of an oil bath. Then, at 55-60° C., with thorough stirring, 92.2 g (1.30 mol) of chlorine gas are introduced through a glass frit, relatively quickly at the beginning and just slowly at the end. HCl gas is evolved. The duration of the introduction is about four to five hours. The reaction is monitored by means of the ¹H-NMR spectrum. The reaction solution is then heated to about 108° C. in order to remove the HCl gas. 150 g of water are then added and the 1,2-dichlorobenzene is removed by steam distillation. About 195 g of 1,2-dichlorobenzene are recovered. 250 g of toluene are added to the hot oil, and the water is then separated off. The yellow isomeric mixture consisting of 2-chloro-1-{3-[4-(2-chloro-2-methyl-proplonyl)-phenyl]-1,1,3-trimethyl-indan-5-yl}-2-methyl-propan-1-one as the main component and 2-chloro-1-{1-[4-(2-chloro-2-methyl-propionyl)-phenyl]-1,3,3-trimethyl-indan-5-yl}-2-methyl-propan-1-one as the subsidiary component is used in the next reaction without being purified further.

3.3) Hydrolysis of the isomeric mixture from the chlorination, consisting of 2-chloro-1-{3-[4-(2-chloro-2-methyl-propionyl)-phenyl]-1,1,3-trimethyl-indan-5-yl}-2-methyl-propan-1-one as the main component and 2-chloro-1-{1-[4-(2-chloro-2-methyl-propionyl)-phenyl]-1,3,3-trimethyl-indan-5-yl}-2-methyl-propan-1-one as the subsidiary component 208 g (0.156 mol) of 30% concentrated NaOH and 208 ml of deionised water and 206 g of methanol are combined in a 1.5 liter reaction flask and heated. There are then added drop-wise at 50° C. in the course of about 30 minutes, with thorough stirring, a total of about 650 ml (0.65 mol tq) of a solution, in toluene, of the isomeric mixture from the preceding chlorination, consisting of 2-chloro-1-{3-[4-(2-chloro-2-methyl-propionyl)-phenyl]-1,1,3-trimethyl-indan-5-yl}-2-methyl-propan-1-one as the main component and 2-chloro-1-{1-[4-(2-chloro-2 -methyl-propionyl)-phenyl]-1,3,3-trimethyl-indan-5-yl}-2-methyl-propan-1-one as the subsidiary component, additionally diluted with 103 g of methanol. The internal temperature slowly rises to 55-60° C. The orange alkaline mixture (about pH 12) is then stirred for about three to four hours at 55-60° C. The conversion is checked with a GC sample and a ¹H-MR sample. The mixture is then heated to 70° C. and stirred for a further five hours. The conversion is again checked with a GC sample and a ¹H-NMR sample. The mixture is then cooled to 45° C. and slowly adjusted to a pH of about 1-2 with about 152 g of 16% hydrochloric acid. The temperature rises by about 7° C. The colour of the emulsion changes from golden yellow to pale yellow. The mixture is then stirred for about one hour at 55-60° C. When the hydrolysis is complete, the reaction mixture is neutralised with a small amount of dilute sodium hydroxide solution. The two phases are separated at about 25° C. in a separating funnel. The organic phase is washed with 200 ml of brine and separated off again. There is no spontaneous crystallisation at room temperature. The organic phase is concentrated in a rotary evaporator. 208.8 g of yellowish oil are obtained and checked with a $^1$H-NMR sample (Example 3.3a)

Elemental Analysis: (408.54)

|  | % C |  | % H |
|---|---|---|---|
| calculated: | 76.44 | calculated: | 7.90 |
| found: | 76.23 | found: | 7.97 |

70 g of toluene are added to 140.4 g of oil, which is dissolved at 50° C. and cooled. After seeding with crystals, crystallisation slowly begins. The suspension is cooled to 5° C. The crystals are then filtered off, washed twice with 30 g of cold toluene and dried in vacuo. There are obtained 72.4 g of white crystals, which melt at 97-105° C. This corresponds to a tq yield of crystals of 54.5% of theory (408.54) over all three reaction steps. In the $^1$H-NMR spectrum there is found an isomeric ratio of about 60% of the main component 2-hydroxy-1-{3-[4-2-hydroxy-2-methyl-propionyl)-phenyl]-1,1,3-trimethyl-indan-5-yl}-2-methyl-propan-1-one and about 40% of the subsidiary component 2-hydroxy-1-{1-[4-(2-hydroxy-2-methyl-propionyl)-phenyl]-1,3,3-trimethyl-indan-5-yl}-2-methyl-propan-1-one. The filtrate is concentrated, and 57.2 g of viscous yellow oil are obtained. This corresponds to a tq yield of oil of 43.1% of theory (408.54) over all three reaction steps. The overall yield of crystals and oil is 97.6% of theory (408.54) over all three reaction steps.

EXAMPLE 4

4.1) Friedel-Crafts reaction Addition of AlCl$_3$ in solid form 153.6 g (0.65 mol) of 1,1,3-trimethyl-3-phenylindan (from Schenectady Prattein Switzerland), 159.3 g (1.495 mol) of isobutyric acid chloride and 203 g of 1,2-dichlorobenzene are placed in a 750 ml reaction flask and cooled to 5-0° C. by means of an Ice bath. In the course of about two to three hours, 208.0 g (1.56 mol) of aluminium chloride are then added in small portions at an internal temperature of 5-0° C. HCl gas is evolved. Stirring is then carried out for about 16 hours at an internal temperature of 0-5° C. At the end of that period, all the aluminium chloride has dissolved. The reddish-yellow reaction mixture is then poured onto ice and water and stirred to complete the reaction. The two phases are separated in a separating funnel. The organic phase is washed with water and then concentrated for a short time in a vacuum rotary evaporator at about 60° C. and about 25 mbar. There are obtained 510.5 g of yellowish oil, an isomeric mixture having 1-[3-(4-isobutyryl-phenyl)-1,1,3-trimethyl-indan-5-yl]-2-methyl-propan-1-one as the main component and 1-[1-4-isobutyryl-phenyl)-1,3,3-trimethyl-indan-5-yl]-2-methyl-propan-1-one as the subsidiary component dissolved in 1,2-dichlorobenzene. Excluding the solvent 1,2-dichlorobenzene, about 60% of the main component and about 40% of the subsidiary component are found in the GC and $^1$H-NMR spectrum. The isomeric mixture is used in the next reaction without being purified further.

4.2) Enol Chlorination 510 g (0.65 mol tq) solution of the isomeric mixture from the Friedel-Crafts reaction having 1-[3-(4-isobutyryl-phenyl)-1,1,3-trimethyl-indan-5-yl]-2-methyl-propan-1-one as the main component and 1-[1-(4-isobutyryl-phenyl)-1,3,3-trimethyl-indan-5-yl]-2-methyl-propan-1-one as the subsidiary component are placed in a 750 ml reaction flask and heated to 60-65° C. by means of an oil bath. Then, at 60-65° C., with thorough stirring, 94.3 g (1.33 mol) of chlorine gas are introduced through a glass frit, relatively quickly at the beginning and just slowly at the end. HCl gas is evolved. The duration of the introduction is about four to five hours. The reaction is monitored by means of the $^1$H-NMR spectrum. The colourless reaction solution is then heated to about 100° C. in order to remove the HCl gas. 100 g of water are then added and the 1,2-dichlorobenzene is removed by steam distillation. About 195 g of 1,2-dichloro-benzene are recovered. 250 g of toluene are added to the hot oil, and the water is then separated off. The isomeric mixture consisting of 2-chloro-1-{3-[4-(2-chloro-2-methyl-propionyl)-phenyl]-1,1,3-trimethyl-indan-5-yl}-2-methyl-propan-1-one as the main component and 2-chloro-1-{1-[4-(2-chloro-2-methyl-proplonyl)-phenyl]-1,3,3-trimethyl-indan-5-yl}-2-methyl-propan-1-one as the subsidiary component is used in the next reaction without being purified further.

4.3) Hydrolysis of the isomeric mixture from the chlorination, consisting of 2-chloro-1-{3-[4-(2-chloro-2-methyl-propionyl)-phenyl]-1,1,3-trimethyl-indan-5-yl}-2-methyl-propan-1-one as the main component and 2-chloro-1-{1-[4-(2-chloro-2-methyl-propionyl)-phenyl]-1,3,3-trimethyl-indan -yl}-2-methyl-propan-1-one as the subsidiary component 208 g (0.156 mol) of 30% concentrated NaOH and 208 ml of deionised water and 206 g of methanol are combined in a 1.5 liter reaction flask and heated. There are then added drop-wise at 50° C. in the course of about 30 minutes, with thorough stirring, a total of about 650 ml (0.65 mol tq) of a solution, in toluene, of the isomeric mixture from the preceding chlorination consisting of 2-chloro-1-{3-[4-(2-chloro-2-methyl-propionyl)-phenyl]-1,1,3-trimethyl-indan-5-yl}-2-methyl-propan-1-one as the main component and 2-chloro-1-{1-[4-(2-chloro-2-methyl-proplonyl)-phenyl]-1,3,3-trimethyl-indan-5-yl}-2-methyl-propan-1-one as the subsidiary component, additionally diluted with 103 g of methanol. The internal temperature slowly rises to 55-60° C. The orange alkaline mixture (about pH 12) is then stirred for about six to seven hours at 65-70° C. The conversion is checked with a GC sample and a $^1$H-NMR sample. The yellow mixture is then cooled to 30° C. and slowly adjusted to a pH of about 1-2 with about 89.4 g of 16% hydrochloric acid. The temperature rises by about 7° C. The colour of the emulsion changes from yellow to pale yellow. The mixture is then stirred for about one hour at 55-60°C. When the hydrolysis is complete, the reaction mixture is neutralised with a small amount of dilute sodium hydroxide solution. The two phases are separated at about 35° C. in a separating funnel. The organic phase is washed with 200 ml of brine and separated off again. There is no spontaneous crystallisation at room temperature. The organic phase is concentrated in a rotary evaporator. 332 g of yellowish oil are obtained and checked with a $^1$H-NMR sample.

65 g of toluene are added to the 332 g of oil, which is dissolved at 40° C. and stirred. After seeding with 0.1 g of crystals, crystallisation slowly begins. On the following day, the slightly yellowish suspension is cooled to 10° C. The crystals are then filtered off, washed twice with 30 g of cold toluene and dried in vacuo. There are obtained 176.8 g of white crystals, which melt at 93-103° C. This corresponds to a tq yield of crystals of 66.6% of theory (408.54) over all three reaction steps. The filtrate is concentrated, and 63.4 g of viscous yellowish oil are obtained. (Example 4.3b) This corresponds to a tq yield of oil of 23.9% of theory (408.54)

over all three reaction steps. The overall yield of crystals and oil is 90.5% of theory (408.54) over all three reaction steps.

The 176.8 g of white crystals are again dissolved at 80° C. in 90 g of toluene, cooled and seeded at room temperature. Crystallization slowly begins. After 48 hours' stirring, the thick mass is diluted with 45 g of toluene and then filtered. The crystals are washed with 120 g of toluene and dried in vacuo at about 50° C. There are obtained 138.8 g of white crystals, which melt at 101.5-107° C. The filtrate is concentrated and 37.6 g of viscous yellowish oil are obtained. (Example 4.3 c) in the $^1$H-NMR spectrum of the crystals and of the oil there is found an isomeric ratio of about 60% of the main component 2-hydroxy-1-{3-[4-(2-hydroxy-2-methyl-propionyl)-phenyl]-1,1,3-trimethyl-indan-5-yl}-2-methyl-propan-1-one and about 40% of the subsidiary component 2-hydroxy-1-{1-[4-(2-hydroxy-2-methyl-propionyl)-phenyl]-1,3,3-trimethyl-indan-5-yl}-2-methyl-propan-1-one. (Example 4.3d)

Elemental Analysis of the Crystals: (408.54)

|  | % C |  | % H |
|---|---|---|---|
| calculated: | 76.44 | calculated: | 7.90 |
| found: | 76.42 | found: | 7.96 |

APPLICATION EXAMPLES

Example A1

UV-Curable Overprint Coating

The 1-phenylindan according to the invention were tested for their suitability as photoinitiators in a UV-curable overprint coating (OPV) and compared with a commercially available product (Esacure KIP 150, Lamberti). The composition of the OPV is shown in the table below.

| Component | % by weight |
|---|---|
| Ebecryl 605 | 35.0 |
| Ebecryl 40 | 10.0 |
| OTA 480 | 30.0 |
| TPGDA | 24.0 |
| Ebecryl 1360 | 0.5 |
| Dow Corning 57 | 0.5 |
| Σ | 100.0 |

OTA 480: glycerol propoxylate triacrylate (UCB)
TPGDA: tripropylene glycol diacrytate (UCB)
Ebecryl 605: bisphenol A epoxyacrylate, diluted with 25% TPGDA (UCB)
Ebecryl 40: pentaerythritol ethoxylate tetraacrylate (UCB)
Ebecryl 1360: hexafunctional silicone acrylate (UCB)
Dow Corning 57: silicone additive, flow improver (Dow Corning)

0.6 g and 0.8 g of each photoinitiator was weighed in per 10 g of formulation. The samples were applied by means of a knife to white card in a layer thickness of 6 µm and then exposed by means of a UV exposure device (IST) under two medium-pressure mercury lamps each of 120 W/cm. Immediately after the exposure, the resistance of the coating surface to wiping was determined by means of a paper towel. The curing speed is the maximum conveyor belt speed, in m/min, of the exposure device at which the coating surface remains resistant to wiping.

The yellowing of the overprint coatings (b* values) was determined 15 minutes after the exposure as well as after an additional UV exposure (TLK 40/05 fluorescent tube) over a period of 22 hours. For that purpose, the samples were applied by means of a knife to white-coated chipboard in a layer thickness of 100 µm and cured at a conveyor belt speed of 10 m/min. A CM-508 i spectrophotometer (Minolta) was used for measuring the b* values. The results obtained are shown in the following table.

| Photoinitiator | Curing speed [m/min] | | Yellowing[1] | |
|---|---|---|---|---|
| Example | 6% initiator | 8% initiator | b* (0)[2] | b* (22)[3] |
| Esacure KIP 150 | 30 | 60 | 6.4 | 5.7 |
| Example 1.4 | 30 | 60 | 5.5 | 5.2 |
| Example 1.3 | 30 | 70 | 5.0 | 4.7 |
| Example 3.3a | 25 | 60 | 5.5 | 6.9 |
| Example 4.3b | 25 | 50 | 6.2 | 8.4 |
| Example 4.3c | 30 | 50 | 6.1 | 8.0 |
| Example 4.3d | 40 | 70 | 5.9 | 4.9 |

[1]Determined for an initiator concentration of 6%.
[2]Measured 15 minutes after the exposure.
[3]Measured after 22 hours' additional UV exposure (TLK 40/05 fluorescent tube).

In the tested UV-curable overprint coating, the same curing effectiveness is observed for the 1-phenylindan according to the invention of Examples 1.3 and 1.4 as for the commercial photoinitiator Esacure KIP 150. With regard to yellowing, the compounds of Examples 1.3 and 1.4 and 4.3d tend to result in lower values than Esacure KIP 150.

Example A2

Epoxy Acrylate Clear Coat

Formulation:
89.0% by weight Ebecryl 604 (75% epoxy acrylate in hexanediol diacrylate, UCB)
10.0% by weight Sartomer SR 344 (polyethylene glycol 400 diacylate, Cray Valley)
1.0% by weight Ebecryl 350 (silicone diacrylate, UCB)

The coatings were applied with a 6 µm (spiral coater No. 1 yellow) coater to aluminum sheets. They were cured with two 80 W/cm medium pressure mercury lamps at the maximum curing speed which is possible to obtain a through-cure and tack-free surface. The results are shown in the Table below (curing speed m/min).

The coatings were applied to chipboard (100 µm) and cured at a belt speed of 10 m/min to determine the pendulum hardness, b* value (yellowing) and gloss after an exposure time of 30 minutes at ambient temperature. The photoinitiator concentration is 2%.

| Photoinitiator 2% | Curing Speed (m/min) | Pendulum hardness (s) | DE* gloss | Db* yellowing |
|---|---|---|---|---|
| ESACURE KIP 150 | 45 | 192 | 3.3 | 3.1 |
| Example 1.4 | 45 | 192 | 3.1 | 2.9 |
| Example 1.3 | 35 | 196 | 3.0 | 2.8 |
| Example 3.3a | 40 | 192 | 3.0 | 2.8 |
| Example 4.3b | 35 | 192 | 3.4 | 3.3 |
| Example 4.3c | 35 | 193 | 3.4 | 3.3 |
| Example 4.3d | 50 | 189 | 3.1 | 3.0 |

What is claimed is:

1. A process for the preparation of a crystalline isomeric mixture of compounds of formulae I and II

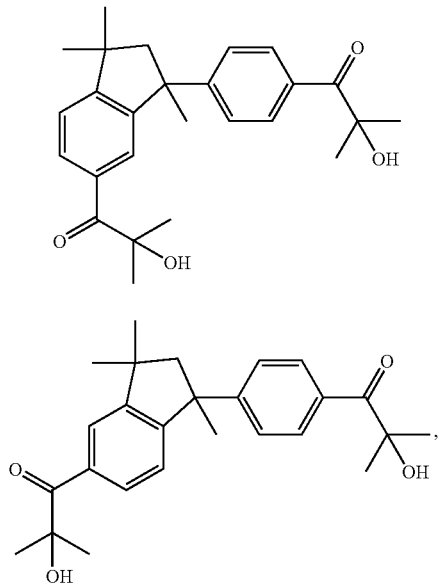

which process comprises the following steps:

a) the slow addition of aluminium chloride, in portions in the course of from 2 to 3 hours, so that a local overdosing of aluminium chloride is avoided, to a solution comprising 1,1,3-trimethyl-3-phenylindan having a low oligomer content and isobutyric acid halide in 2-dichlorobenzene at a reaction temperature of from 0° C. to 5° C., an isomeric mixture consisting of compounds of formulae Ia and IIa being obtained

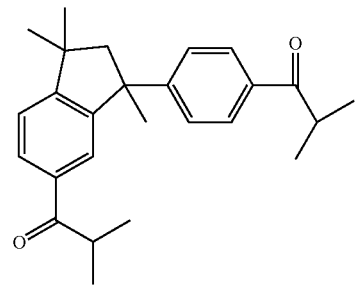

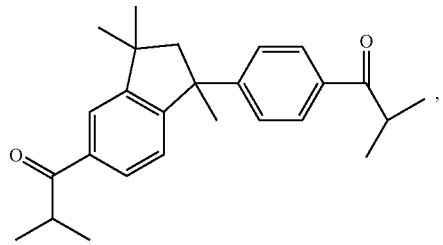

b) enol chlorination of compounds Ia and IIa, an isomeric mixture consisting of compounds of formulae Ib and IIb being obtained

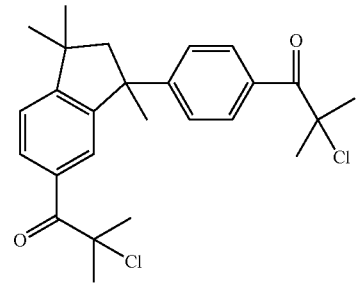

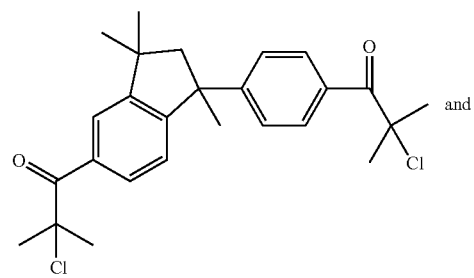

c) hydrolysis of the chlorinated isomeric mixture from step b).

2. A process for the preparation of a crystalline compound of formula I

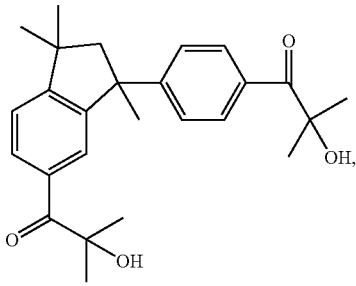

which process comprises a) the slow addition of aluminium chloride, in portions in the course of from 2 to 3 hours, so that a local overdosing of aluminium chloride is avoided, to a solution comprising 1,1,3-trimethyl-3phenylindan having a low oligomer content and isobutyric acid halide in 12-dichlorobenzene at a reaction temperature of from 0° C. to 5° C., an isomeric mixture consisting of compounds of formulae Ia and IIa being obtained

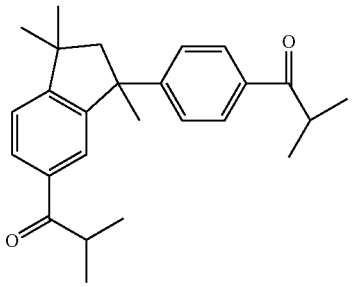

-continued

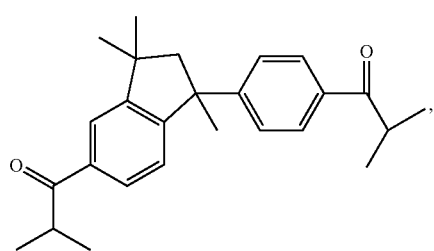
IIa b) enol chlorination of compounds Ia and IIa, an isomeric mixture consisting of compounds of formulae Ib and IIb being obtained

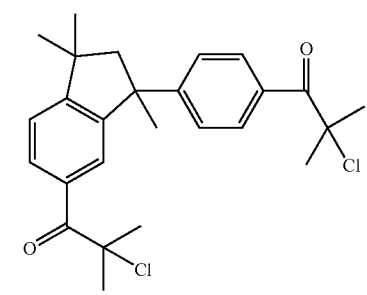
Ib

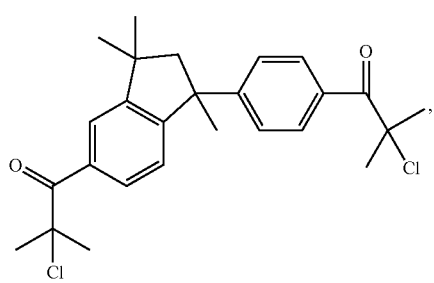
IIb c) separation of the compound of formula Ib by recrystallisation and d) hydrolysis of compound Ib.

3. A process for the preparation of a crystalline compound of formula II

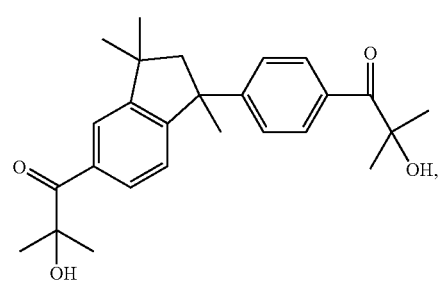
II which process comprises a) the slow addition of aluminium chloride, in portions in the course of from 2 to 3 hours, so that a local overdosing of aluminium chloride is avoided, to a solution comprising 1,1,3-trimethyl-3-phenylindan having a low oligomer content and isobutyric acid halide in 12-dichlorobenzene at a reaction temperature of from 0° C. to 5° C., an isomeric mixture consisting of compounds of formulae Ia and IIa being obtained

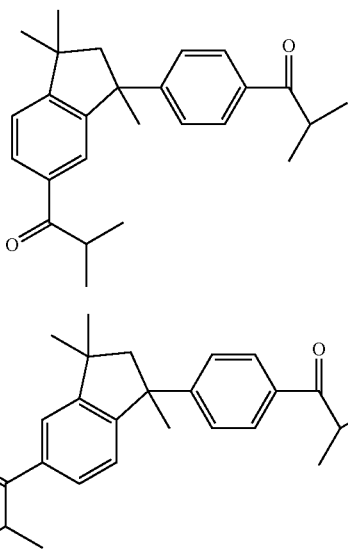
Ia

IIa b) enol chlorination of compounds Ia and IIa, an isomeric mixture consisting of compounds of formulae Ib and IIb being obtained

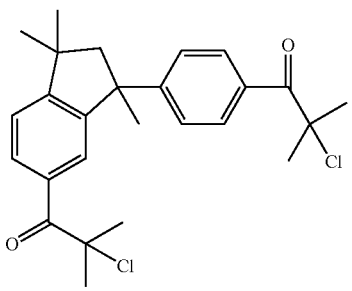
Ib

IIb c) separation of the compound of formula Ib by recrystallisation and d) hydrolysis of compound IIb.

4. A process according to claim 1, wherein pure 1,1,3-trimethyl-3-phenylindan and isobutyric acid halide are first brought together and aluminium chloride is metered in slowly in the course of from 2 to 3 hours, so that a local overdosing of aluminium chloride is avoided.

5. A process according to claim 2, wherein pure 1,1,3-trimethyl-3-phenylindan and isobutyric acid halide are first brought together and aluminium chloride is metered in slowly in the course of from 2 to 3 hours, so that a local overdosing of aluminium chloride is avoided.

6. A process according to claim 3, wherein pure 1,1,3-trimethyl-3-phenylindan and isobutyric acid halide are first brought together and aluminium chloride is metered in slowly in the course of from 2 to 3 hours, so that a local overdosing of aluminium chloride is avoided.

* * * * *